United States Patent [19]

Feuillet

[11] Patent Number: 5,091,141
[45] Date of Patent: Feb. 25, 1992

[54] DEVICE FOR INSERTING AND POSITIONING A TOOL INSIDE A HEAT EXCHANGER AND USE OF THIS DEVICE

[75] Inventor: Patrice Feuillet, Marcy L'Etoile, France

[73] Assignee: Framatome, Courbevoie, France

[21] Appl. No.: 527,554

[22] Filed: May 23, 1990

[30] Foreign Application Priority Data

May 23, 1989 [FR] France ................. 89 06726

[51] Int. Cl.$^5$ ............................................. G21C 19/00
[52] U.S. Cl. ...................................... 376/260; 376/310
[58] Field of Search .......................... 376/310, 245, 260; 122/381, 382, 392; 165/95; 15/104.062, 104.05, 104.9

[56] References Cited

U.S. PATENT DOCUMENTS

| | | | |
|---|---|---|---|
| 3,546,961 | 12/1970 | Marton et al. ................. | 74/501 |
| 4,424,769 | 1/1984 | Charamathieu et al. ........ | 376/310 |
| 4,757,785 | 7/1988 | Klahn et al. ................... | 376/310 |
| 4,765,947 | 8/1988 | Babin et al. ................... | 376/245 |
| 4,980,120 | 12/1990 | Bowman et al. ................ | 376/310 |

FOREIGN PATENT DOCUMENTS

| | | |
|---|---|---|
| 0147648 | 11/1984 | European Pat. Off. . |
| 723746 | 8/1942 | Fed. Rep. of Germany . |
| 40783 | 9/1931 | France . |
| 53931 | 3/1945 | France . |
| 2613835 | 4/1987 | France . |

Primary Examiner—Brooks H. Hunt
Assistant Examiner—Frederick H. Voss
Attorney, Agent, or Firm—Pollock, Vande Sande & Priddy

[57] ABSTRACT

The device comprises an elongate transmission member (30) which can be moved inside the steam generator tube by pulling and pushing. The elongate member (30) comprises a central metal cable (31), a flexible peripheral sheath (32) and a plurality of annular members (33) which are not connected together and are threaded in sequence onto the flexible sheath (32). A clearance (34) corresponding to the difference in length between the sheath (32) and the total length of the members (33) when they are placed end to end allows the member (30) to be moved inside the tube by pushing without the application of great force. In particular, the device enables heating elements to be inserted and positioned in the curved parts of the tbes of the bundle of a steam generator of a pressurized-water nuclear reactor.

10 Claims, 3 Drawing Sheets

DEVICE FOR INSERTING AND POSITIONING A TOOL INSIDE A HEAT EXCHANGER AND USE OF THIS DEVICE

FIELD OF THE INVENTION

The invention relates to a device for inserting and positioning a tool inside a curved part of a steam generator tube.

BACKGROUND OF THE INVENTION

The steam generators of pressurized-water nuclear reactors comprise a bundle of tubes bent into a U shape and comprising two straight legs whose ends are fixed in a circular tube plate.

The two straight legs of each of the tubes are joined by a curved part whose radius of curvature depends on the position of the tube in the bundle. The bundle comprises tubes whose ends are fixed in openings passing through the tube plate in regions at various distances from its periphery. The tubes whose ends pass through the tube plate near its periphery comprise a curved part with a large radius of curvature, whereas the tubes passing through the tube plate near its central part comprise a curved part with a very small radius of curvature.

The various curved parts of the tubes of the bundle are placed in adjacent positions and form the upper part of the bundle.

The tube plate comprises an entry face with which the ends of the tubes of the bundle are level, this entry face of the tube plate forming the upper wall of a water box arranged in the lower part of the steam generator.

The water box is divided by a partition into two parts and each of the tubes of the bundle opens out into one of the parts of the water box via one of its ends and into the other part of the water box via its other end. The pressurized water of the nuclear reactor is injected into one of the parts of the water box which is responsible for distributing it into the tubes of the bundle; after circulating in the tubes, this pressurized water is then collected in the second part of the water box.

For steam generator repair or maintenance operations, it may be necessary to insert a tool or a measuring or monitoring device into a tube of the bundle or into a certain number of tubes in succession.

For example, in order to reduce the corrosion sensitivity of the curved parts of the tubes of the bundle, the stress in this curved part is relieved by inserting inside the tube an electrical heating element which is positioned in the curve and is then supplied with electrical current.

These operations are performed on the steam generators of nuclear reactors, which are contaminated after the reactor has been in operation for some time.

It is therefore necessary to perform the insertion and the positioning of the heating elements in the curves of the tubes of the bundle from a distance and from outside the water box of the steam generator.

This is done by employing a means for pulling and pushing, extended by a guide conduit which can be inserted into the water box and positioned in the extension of any tube of the bundle by a device such as a manipulator arm, arranged inside the water box. The means of pulling and pushing allows a flexible transmission member of elongate shape to be moved inside the guide conduit and into any tube of the bundle from outside the water box. The transmission member comprises an end fitted with a coupling which is inserted into, and then moved in, the tube by pushing until this coupling reemerges from the other end of the tube into which it was inserted.

An additional guiding means makes it possible to recover the end of the transmission member comprising the coupling at an opening of the water box.

An electrical heating element is attached to the coupling outside the water box and is then inserted into the tube by pulling on the transmission member which drags the electrical heating element by means of the coupling.

The pulling movement is performed over a sufficient length to position the electrical heating element along the entire length of the curve in which the stress relieving is performed.

The elongate transmission member which is moved by pushing and by pulling inside the tubes of the bundle, and which is generally referred to by those skilled in the art as a "rabbit", comprises a sheath whose external diameter is smaller than the internal diameter of a tube. Satisfactory guidance of the rabbit inside the tube is thus obtained.

However, a device of this kind does not allow the push to be transmitted in a wholly satisfactory manner when it is being positioned The rabbit tends to bend in successive sections and to jam inside the tube, this phenomenon being known as "snaking". The friction of the rabbit's sheath inside the tube increases until it is no longer possible to continue the movement by pushing. These problems increase with the length of the tubes along which the rabbit is to be moved.

It is possible to avoid these disadvantages to some extent by taking precautions when the rabbit is being moved and by performing this movement very slowly. As a result, the positioning of the rabbit is tricky and increases the time of exposure of the operators to the radiation originating from the steam generator.

Moreover, when the tool is positioned in the curve by pulling the rabbit, the latter tends to lengthen because of the considerable friction between the sheath and the inner surface of the steam generator tube. It is therefore very difficult to position the tool accurately in the curved part of the tube. This defective positioning entails a risk of compromising the satisfactory progress of the operation performed by the tool.

Friction between the sheath of the rabbit and the internal surface of the tube requires very large pulling forces, particularly in the case of the curved parts of small radius of curvature which are situated in the central part of the bundle In this case, it becomes difficult, or even impossible, to position correctly a tool such as a heating element inside the curve.

SUMMARY OF THE INVENTION

The object of the invention is therefore to provide a device for inserting and positioning a tool inside a tube of a heat exchanger such as a steam generator, comprising a bundle of tubes bent into a U shape, each having two straight legs whose ends are fixed in holes passing through a tube plate and a curved part joining the two straight legs and, on one side of the tube plate, a water box bounded by one face of the tube plate onto which the ends of the tubes open out, the insertion device comprising, outside the water box, a means of pulling and pushing; a guide conduit connected to an exit end of the means of pulling and pushing entering the water box and connected to a device for positioning the guide conduit in concordance with an end of any tube opening of the tube plate and a transmission member of elongate shape, engaged in the means of pulling and pushing to move it inside the guide conduit and a tube of the bundle, comprising a coupling for the tool at one of its ends, this device making it possible to position a tool simply, rapidly and with very great accuracy, in any part of a steam generator tube, and in particular in a curved part of a small radius of curvature.

For this purpose, the elongate transmission member comprises a central cable, a flexible peripheral sheath whose external diameter is smaller than the internal diameter of a tube of the bundle, and a plurality of annular members whose internal diameter is greater than the external diameter of the sheath and whose external diameter is smaller than the internal diameter of a tube of the bundle. The annular members are not connected together and are threaded in sequence onto the flexible sheath of the transmission member, in such a number that the total length of the tubular members when they are placed end to end is less than the length of the flexible sheath by an amount which is substantially equal to the length of an annular member.

BRIEF DESCRIPTION OF THE DRAWINGS

In order that the invention may be more clearly understood, a description will now be given, by way of example, with reference to the attached drawings of several embodiments of a device in accordance with the invention.

DETAILED DESCRIPTION

Figure 1:
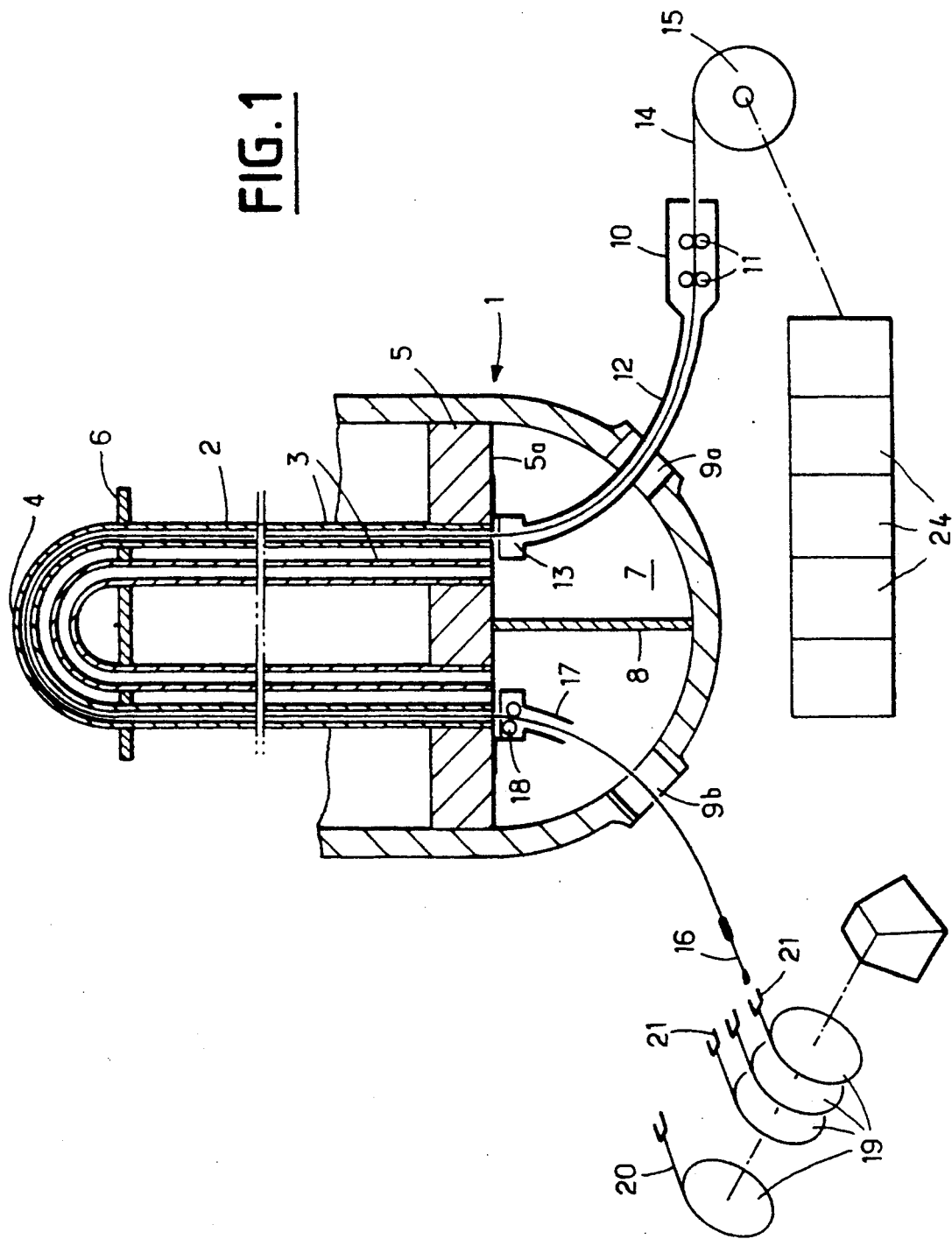
FIG. 1 is a general elevation view, in partly in section, of a device for inserting and positioning electrical heating elements in the curved parts of the tubes of a steam generator.

FIG. 1 shows the lower part of a steam generator 1 and a part of the bundle 2 of this steam generator, consisting of tubes 3 bent into a U shape. Each of the tubes 3 of the bundle comprises two straight legs whose ends are fixed in holes passing through the tube plate 5 of the steam generator and a curved part 4 arranged in the upper part of the bundle.

The tubes 3 are held in a regular arrangement in the bundle by spacer plates such as 6, distributed uniformly along the length of the straight legs of the tubes.

The ends of the straight legs of the tubes 3 are level with the lower face 5a of the tube plate 5 forming its entry face. The face 5a of the tube plate forms the upper wall of a water box 7 of hemispherical shape, divided into two parts by a partition 8.

Each of the tubes 3 of the bundle comprises a first end opening out into a first part of the water box and a second end opening out into the second part of the water box.

In FIG. 1 the steam generator 1 has been shown during positioning of a tool consisting of a heating element inside a tube of the bundle.

This operation is performed during a stoppage of the nuclear reactor, the steam generator being cold and empty of water.

The water box 7 comprises two manholes 9a and 9b passing through its wall, one on each side of its partition 8.

While the reactor is in operation, these manholes are closed by leakproof closure plates; on the other hand, during the stoppage periods of the nuclear reactor, these plates are removed to permit the insertion of tools for working inside the water box of the steam generator, in order to carry out the maintenance and the repair of the steam generator The device for inserting and positioning heating elements which is shown in FIG. 1 comprises a means 10 for pulling and pushing comprising two pairs of motor-driven rolls 11. The means of pulling and pushing 10 is extended at its exit end by a guide conduit 12 which is inserted into the water box 7 of the steam generator through the manhole 9a. The end of the guide conduit 12 remote from the pushing and pulling means 10 is fixed in a carrier device 13 permitting this end of the guide conduit 12 to be placed in the extension of an end of any tube 3 of the bundle.

The carrier device 13, which may be fixed under the tube plate or which may consist of an arm mounted inside the water box, is a piece of equipment which is conventional within the scope of the maintenance operations on steam generators of nuclear reactors.

The device for inserting and positioning a tool which is shown in FIG. 1 additionally comprises an elongate transmission member 14 of a length sufficient to enable the component 14 to be inserted, by means of the guide conduit 12, along the entire length of any tube 3 of the bundle and so as to reemerge through the manhole 9b, as shown in FIG. 1.

The elongate transmission member 14 is stored on a winding and unwinding device 15 situated, near the entry end of the pulling and pushing means 10.

At its end by which the insertion into the tube 3 is performed, the member 14 comprises a conically shaped guiding and coupling component 16.

At the exit end of the tube 3, remote from the entry end situated in the extension of the conduit 12, there is arranged a second guide conduit 17 through which the member 14, passes after having passed through a guiding and measuring device 18.

Near the manhole 9b of the water box 7, there is arranged a battery of reels 19 onto each of which is wound an electrical heating element 20 which can be inserted into a tube 3 of the bundle to relieve the stress in its curved part 4.

At their end, the electrical heating elements 20 comprise a coupling member 21 enabling the heating element 20 to be connected to the guiding and coupling component 16 of a transmission member 14.

The necessary operations for inserting and positioning a heating element in the curved part of a tube 3 of the bundle, which will be described below, are actuated by control and actuation consoles 24 which are connected to the various members of the device and in particular to the winder-unwinder 15 and to the pulling and pushing means 10.

At the start of the operation, the elongate member 14 is wholly wound onto the winder-unwinder 15, the end component 16 remaining accessible outside the winder-unwinder.

The member 14 is inserted into the pulling and pushing means 10 which is switched on to operate in the pushing direction preceded by the end component 16, the member 14 travels forward inside the guide tube 12 and then inside the tube 3, situated in the extension of the conduit 12

The component 16, forming the end of the member 14, reemerges from the exit end of tube 3 and enters the device 18 and then the guide conduit 17, which causes the component 16 to reach the region of the manhole 9b.

The member 14 continues to be moved by pushing until such time as a sufficient length of this flexible member has come out of the water box to make it possible to make the coupling between the component 16 and the coupling device 21 of one of its heating elements 20 which is wound onto a reel 19.

The direction of operation of the pulling and pushing means 10 is then reversed, so as to exert a pull on the member 20 by means of the elongate member 14.

The corresponding reel 19 is made to rotate and the heating element is thus unwound and then inserted into the water box, into the guide conduit 17 and into the tube 3.

The insertion of the heating element into the tube 3 is continued by pulling the elongate transmission member 14 until it has become possible to obtain satisfactory positioning of the heating element in the curve 4. This positioning is checked by measuring the length of the member 14 which has been moved by pulling, starting from a reference position.

Figure 2:
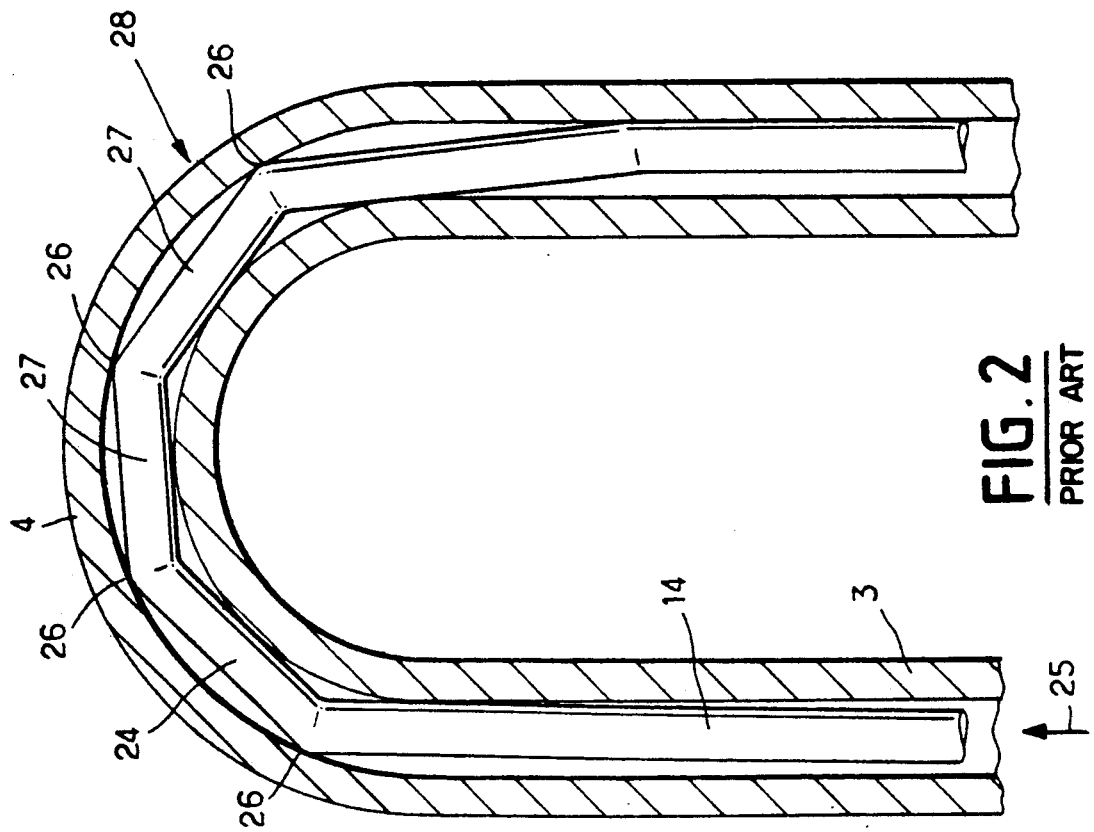
FIG. 2 is a section view a vertical plane of the curved part of a tube into which a rabbit according to the prior art is introduced by pushing.

FIG. 2 shows the curved upper part 4 of a tube 3 of the bundle of a steam generator, during the insertion by pushing of an elongate member 14 consisting of a rabbit according to the prior art. The outer sheath of the rabbit 14 has a diameter which is smaller than the internal diameter of the tube 3 of the bundle.

In order to transmit thrust forces in the axial direction of the tube (arrow 25) by means of the rabbit 14, this rabbit must have a relatively high rigidity, while retaining the flexing characteristics which allow it to pass through the curved parts 4 of small radius of curvature.

It may be necessary, in fact, to apply relatively large thrust forces, insofar as the forces of friction of the sheath of the rabbit on the inner wall of the tube are themselves large during the passage through the curved parts.

Owing to its relative rigidity, the sheath of the rabbit 14 folds in an angular manner, creating fold regions 26, between which the sheath forms rectilinear sections 27.

The pushing force must therefore be great, to overcome the frictional and jamming forces of the sheath inside the curved part 4.

In particular, the pushing force must be extremely large to ensure the passage of the sheath of the rabbit 14 through the end part 28 of the curve 4.

Furthermore, the substantially angularly shaped folds 26 in the sheath of the rabbit 14 produce the risk of causing the breakage of the rabbit, either during its initial movement by pushing, or during the positioning of the tool in the tube by pulling the rabbit.

In either case, it is very difficult to recover, inside the tube, the end part of the rabbit and/or the tool attached to this end part.

Moreover, as indicated above, during the positioning of the tool by pulling the rabbit 14, the latter undergoes a certain elongation when the pulling forces which are applied exceed a certain level In this case, the positioning of the tool in the tube is controlled only approximately.

Figure 3:
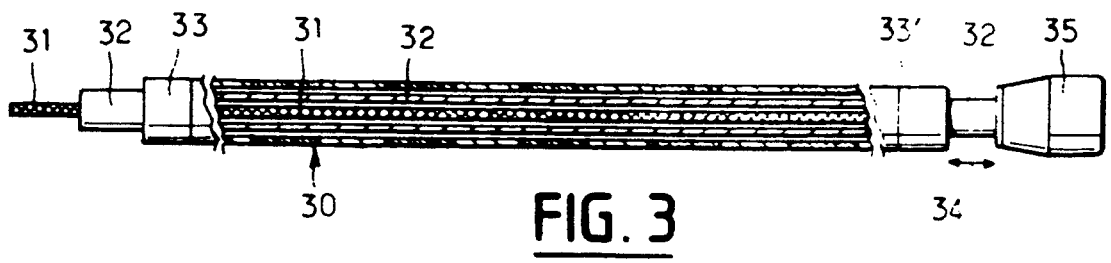
FIG. 3 is a side view, partly in section, of the transmission member of a device according to the invention

FIG. 3 shows the elongate transmission member of a device for inserting and positioning according to invention, enabling the above mentioned disadvantages be overcome.

The elongate transmission member 30 is produced in a coaxial form and comprises a central part 31 consisting of a metal, for example steel, cable, a flexible plastic sheath 32 arranged around the cable 31 and an assembly of angular members 33 threaded onto the flexible sheath 32.

At one of their ends, the cable 31 and the sheath 32 are connected to a conically shaped guiding and coupling component 35 enabling the elongate transmission member to be guided inside a steam generator tube and allowing this elongate transmission member to be connected to a tool such as an electrical heating element.

Figure 4:
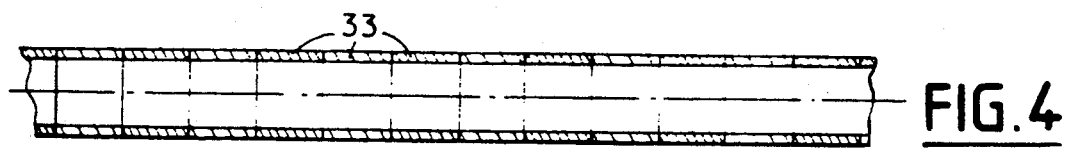
FIG. 4 is a larger-scale view in axial section of the outer part of the transmission member consisting of a stack of annular members

As can be seen in FIGS. 3 and 4, the annular members 33 may consist of straight tube sections arranged in sequence in an adjoining manner.

These annular members 33 have an external diameter which is less than the internal diameter of a steam generator tube and an internal diameter which is larger than the external diameter of the flexible sheath 32. In this way, the annular members 33 are mounted so that they can slide freely over the sheath 32.

The annular members 33 are all identical and have a length which is substantially equal to their external diameter, i.e., smaller than the internal diameter of the steam generator tubes.

In the case of the steam generators of pressurized-water nuclear reactors constructed at the present time, this internal diameter of the tubes of the bundle is about 2 cm.

The annular members 33 are threaded adjoiningly onto the sheath 32 and along its entire length, the number of members employed being defined by the length of the sheath corresponding to the length of the elongate transmission member.

However, as can be seen in FIG. 3, a clearance 34 is provided, whose total amplitude for all the annular members 33 arranged end to end along the length of the sheath 32 has a value which is substantially equal to the length of one of the members 33. In FIG. 3, the members 33 have been shown adjacent over the entire length of the sheath 32, the clearance 34 being seen as a space between the first annular member 33' and the conically shaped component 35.

The annular members 33 is preferably made of a rigid plastic material.

FIGS. 5 to 9 show different embodiments of the annular members forming the outer part of the elongate transmission member of the device for inserting and positioning according to the invention.

Depending on individual cases, the annular members may all be identical or have different and complementary shapes.

Figure 5:
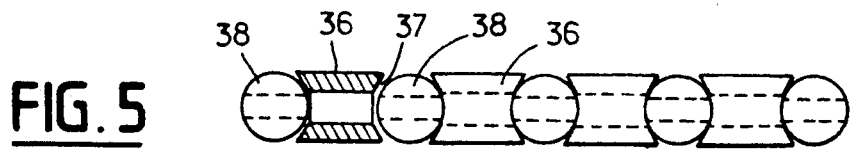
FIG. 5 is a side view, partly in section, of the outer part of a transmission element of a device according to a second embodiment of the invention.

In FIG. 5, the annular members consist successively of cylindrical rings 36 chamfered at their ends 37 and of spherical balls 38, through each of which a bore passes in the radial direction.

The annular members 36 and 38 are threaded one, in an alternating manner, onto the sheath of the elongate transmission member. In this way, the spherical external surfaces of the balls 38 engage, via their part situated at the periphery of the central bore of the ball 38, in the chamfered parts 37 provided at the end of the rings 36.

In this way a very good alignment of the successive annular members in the lengthwise direction of the elongate member can be obtained at the same time as a possibility of deflection of the annular members relative to each other.

The bores of the rings 36 and of the spheres 38 have diameters which are larger than the external diameter of the flexible sheath of the elongate member.

In addition, the rings 36 and the spheres 38 have identical external diameters.

Figure 6:
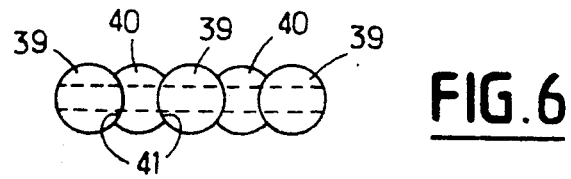
FIG. 6 is a side view of the outer part of the transmission member of a device according to a third embodiment of the invention.

FIG. 6 shows a third embodiment of the annular members forming the outer part of the elongate transmission member.

These annular members consist successively, along the length of the transmission member, of a spherical ball 39 comprising a bore in a radial direction and of a ball 40 comprising two concave spherical caps 41 pointed outwards. A bore also passes through the balls 40 in a radial direction, its diameter being substantially equal to the diameter of the bore of the balls 39; this diameter is larger than the external diameter of the flexible sheath of the elongate transmission member.

When the balls 39 and 40 are threaded successively onto the flexible sheath of the transmission member, the outer surfaces of the balls 39, around the bore in a radial direction, engage in the concave caps 41 of the balls 40 inserted between the balls 39.

In this way, a very good alignment of the assembly of the annular members is obtained along the length of the transmission member, together with a possibility of orienting the members relative to each other.

Figure 7:
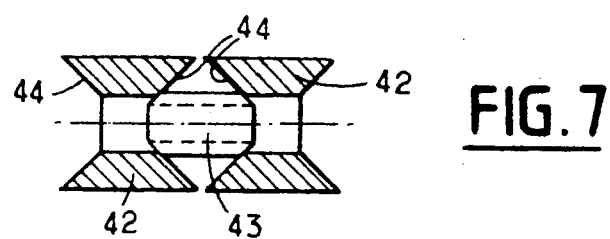
FIG. 7 is a side view, partly in section, of the outer part of the transmission member of a device according to a fourth embodiment of the invention.

FIG. 7 shows annular members 42 and 43 intended to be threaded successively and alternately onto the flexible sheath of an elongate transmission member.

The members 42 consist of rings comprising frustoconical surfaces 44 machined on each of their faces, and the members 43 consist of tubular components chamfered at their ends and inserted between the successive frustoconical surfaces 44 of two components 42, when the members 42 and 43 are threaded onto the sheath of the transmission member.

The rings 42 and the tubular components 43 comprise an internal bore whose diameter is greater than the external diameter of the sheath of the transmission member.

Figure 8:
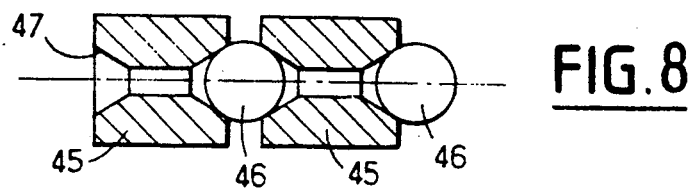
FIG. 8 is a side view, partly in section, of the outer part of a transmission member according to a fifth embodiment of the invention.

FIG. 8 shows annular members 45 and 46 arranged in sequence and alternating along the length of the elongate transmission member.

The members 45 consist of cylindrical rings comprising frustoconical surfaces 47 machined into each of their faces. The members 46, each of which is inserted between two members 45, consist of spheres through which a bore passes in a radial direction, its diameter being greater than the diameter of the flexible sheath of the elongate transmission member. The outer surfaces of the balls 46, around the bore in the radial direction, come into contact with the hollow frustoconical surfaces 47 of the rings 45.

An assembly of annular members is thus obtained step by step, so as to permit their alignment in the lengthwise direction of the elongate member. As before, a possibility of deflecting the members relative to each other is also obtained, to ensure passage through the curved parts of the tubes.

Figure 9:
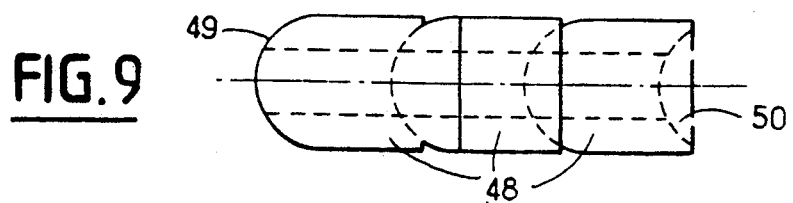
FIG. 9 is a side view of the outer part of a transmission member of a device according to a sixth embodiment of the invention.

FIG. 9 shows successive annular members 48 which are all identical and which consist of cylindrical rings one end of which has the shape of a convex spherical cap 49 and the other end of which comprises a hollow part 50 in the shape of a concave spherical cap. The members 48 comprise an internal bore whose diameter is greater than the external diameter of the flexible sheath of the elongate transmission member.

When the members 48 are threaded in sequence onto the flexible sheath of the elongate member, the ends 49 in the shape of a convex spherical cap engage in the hollow parts 50 in the shape of a concave spherical cap so as to ensure a mutual fit and an assembly of the members 48 with a very good alignment in the axial direction of the elongate member, while retaining a possibility of deflecting the members relative to one another, to permit the passage of the transmission member through the curved parts of the tubes.

Figure 10:
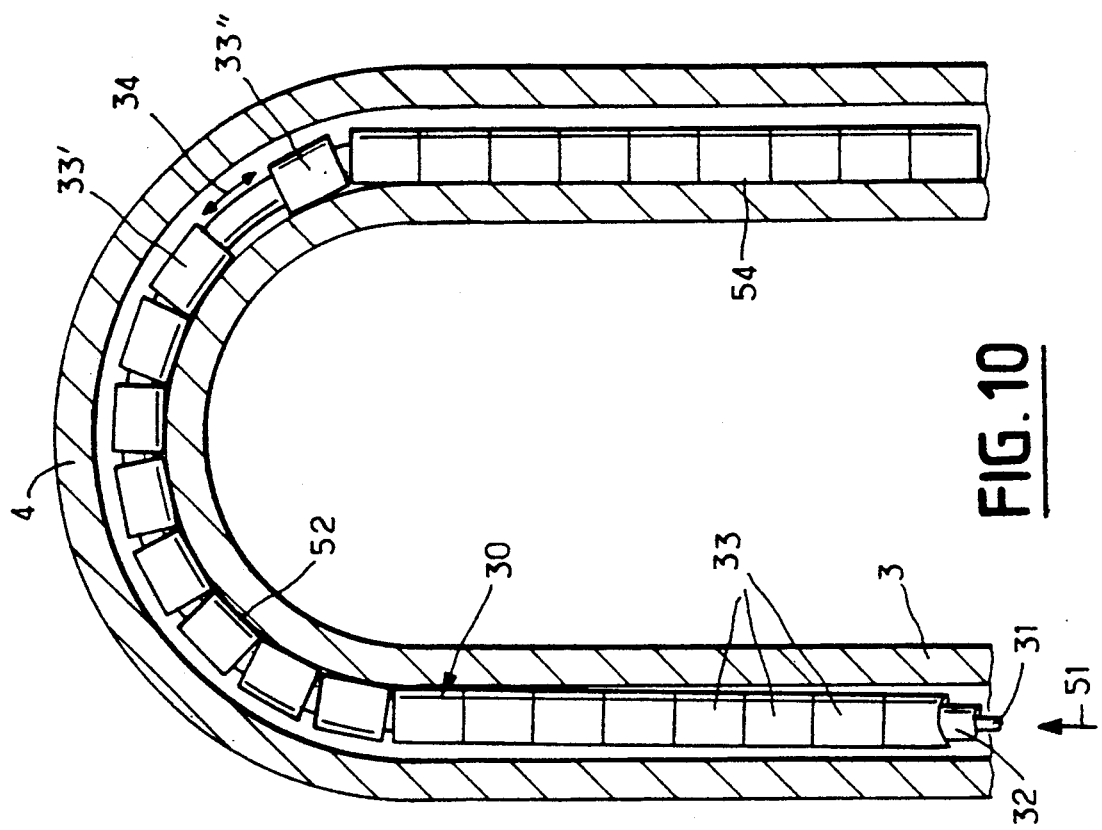
FIG. 10 is a view in section through a vertical plane of the curved part of a steam generator tube in which a transmission member of a device according to the invention is arranged.

FIG. 10 shows an elongate transmission member 30 of a device for inserting and positioning a tool according to the invention, inside a curved part 4 of a small radius of curvature of a steam generator tube 3 during the movement of the member 30 by pushing inside the tube 3.

The thrust is exerted in the direction and the orientation of arrow 51, i.e., in the axial direction of the tube 3.

The annular members forming the external part of the transmission member 30 consist of rings 33 such as shown in FIGS. 3 and 4.

The central part of the elongate member consisting of the cable 31 and the sheath 32 has a flexibility which enables it to match perfectly the shape of the curved part 4 of the tube 3. In addition, this central part has a diameter which is substantially smaller than the internal diameter of the tube 3, with the result that no frictional contact is produced between the sheath 32 and the internal surface of the tube 3 in the curved part 4.

The annular members 33 arranged around the central part provide the guidance of the elongate member as it moves in the tube. These annular members, made of plastic, are not capable of damaging the internal surface of the tube by friction. Moreover, as can be seen in FIG. 10, these members are capable of pivoting slightly relative to each other, to accommodate the curvature of the curved part 4. Each of the annular members 33 bears on the inner surface of the tube 3 along a generatrix 52 whose direction enables the shape of the curve to be matched perfectly.

During the movement of the elongate transmission member 30 inside the tube 3, the thrust exerted on the rings 33 which are stacked on each other causes them to move in the straight part of the tube preceding the curved part 4, and in this curved part.

On leaving the curved part 4, the annular members 33 stack on each other in the straight part of the tube which is situated following the curved part 4, to form a column 54, in which the annular members 33 about against each other.

The clearance 34 corresponding to the difference in length between the central part of the elongate member and the succession of annular members is found again at the exit of the curved part 4, between the last annular member 33' to which the thrust is applied and the upper member 33" of the column 54. The members 33 change from position 33' to 33" under the effect of gravity.

The clearance 34, whose value corresponds substantially to the length of an annular member 33, makes it possible to obtain a certain flexibility of the central part of the transmission member consisting of the cable 31 and the sheath 32.

The thrust needed to move the elongate transmission member 30 inside the tube 3 can thus be limited to a low level, since the elongate member has a flexibility which allows it to match the form of the curves of the tubes, since no major friction is produced between the outer surface of this elongate member and the internal surface of the tube and since the guidance of the elongate member is nevertheless ensured in an effective manner.

When the end of the elongate transmission member comprising the nose cone 35 reaches a position which enables it to be fastened to the end of the tool to be inserted into the tube, this coupling is performed and the direction of actuation of the device for pulling and pushing is then changed The pull applied to the elongate member is transmitted by means of the central metal cable 31, which does not undergo any appreciable elongation. The tool can therefore be placed in the curve 4 in an extremely accurate manner In this stage of movement by pulling, the annular members 33 play no active part.

The transmission member of the device according to the invention exhibits very good rigidity in compression when pushed, insofar as the flexible central part is surrounded by a succession of rigid rings. Furthermore, this elongate member exhibits very good flexural characteristics, since its central part is flexible and since its outer part consists of rings which are capable of pivoting relative to each other in the curved parts of the tube.

The elongate member of the device according to the invention also exhibits a very good resistance to being distorted by pulling, by virtue of the metal cable forming the core of its flexible central part.

When a pulling force is applied to the rings of the transmission member by a pull-push device, for example of the type incorporating rollers, self-jamming of the rings on the central part of the transmission member is produced, and this improves the force transmission conditions and the ease of inserting the transmission member into the tube.

Wires or cables such as electrical conductors can be passed between the metal cable and the sheath of the central part of the transmission member. In this way it is possible, for example, to fit a camera or a Foucault current probe or an ultrasonic probe at the end of the transmission member.

The annular members forming the outer part of the elongate transmission member of the device may differ in shape from those which have been described It is quite obvious that the means of pulling and pushing the elongate member will need to comprise driving members designed to interact with the annular members chosen to form the outer part of the transmission member.

In the case of the steam generators of pressurized-water nuclear reactors, the elongate transmission member will need to have a length of the order of 40 m.

The device for inserting and for positioning according to the invention can be employed successively in different tubes of the steam generator bundle for positioning tools in each of these tubes It will be possible to use the tools simultaneously after their positioning.

The device according to the invention makes it possible to position tools both in tubes which have curves of a large diameter, of the order of 6 m, and in tubes which have small curves whose diameter is approximately 10 cm.

The tools positioned may be of any type and can be employed to perform any operation inside the tube.

The invention applies to any steam generator comprising tubes which have a curved part joining two legs of great length The device can be employed to perform an operation in a heat exchanger tube other than a steam generator tube of a pressurized-water nuclear reactor.

I claim:

1. In a heat exchanger comprising a bundle of tubes (2) bent into a U shape, each of said tubes having two straight legs whose ends are fixed in holes passing through a tube plate (5) and a curved part (4) joining said two straight legs and, on one side of said tube plate (5), a water box (7) bounded by a face (5a) of said tube plate onto which ends of said tubes (3) open out, a device for inserting and positioning a tool inside a tube (3) comprising, outside said water box (7), a means (10) for pulling and pushing a guide conduit (12) connected to an exit end of said means for pulling and pushing (10), said guide conduit entering said water box (7) and being connected to a device (13) for positioning said guide conduit (12) in concordance with an end of any tube (3) opening out of said tube plate (5) and a transmission member (14) of elongate shape engaged in said means (10) for pulling and pushing to move it inside said guide conduit (12) and a tube (3) of said bundle comprising a component (16) for coupling to said tool (20) at an end of said tool, and wherein said elongate transmission member (14, 20) comprises a central metal cable (31), a flexible peripheral sheath (32) having an external diameter smaller than an internal diameter of a tube of said bundle and a plurality of annular members (33) having an internal diameter larger than an external diameter of said sheath (32) and an external diameter smaller than said internal diameter of a tube of said bundle (3), said annular members being unjoined and being threaded in sequence onto said flexible sheath (32) of said transmission member in a number such that a total length of said annular members (33) when placed end to end is smaller than a length of said flexible sheath (32) by a length which is substantially equal to a length of a single said annular member (33).

2. Device according to claim 1, wherein said annular members (33) are all identical.

3. Device according to claim 2, wherein said annular members (33) consist of tube sections bounded by vertical cross-section planes.

4. Device according to claim 2, wherein said annular members (48) consist of cylindrical tubular components which have one end (49) consisting of a convex spherical surface and an opposite end (50) consisting of a concave spherical surface of a same radius as said convex spherical surface.

5. Device according to claim 1, wherein said annular members (36, 38, 39, 40, 42, 43, 45, 46) are of two different type and are arranged in an alternating manner along the length of said elongate transmission member (30).

6. Device according to claim 5, wherein said annular members (36) of a first type consist of cylindrical tubular components having concave chamfered ends (37) and said annular members of a second type (38) of spherical balls through which a bore passes in a radial direction.

7. Device according to claim 5, wherein said annular members (39) of a first type consist of spherical balls through which a bore passes in a radial direction and said annular members (40) of a second type consist of spherical balls through which a bore passes in a radial direction and comprising, around the central bore, two engaging parts in a shape of a concave spherical cap (41).

8. Device according to claim 5, wherein said annular members (42) of a first type consist of rings comprising a frusto-conical engagement surface (44) on each of their faces and said annular members of a second type consist of tubular components (43) comprising chamfered end parts capable of engaging in facing engagement surfaces (44) of two members (42) of said first type.

9. Device according to claim 5, wherein said annular members (45) of a first type (45) consist of rings comprising a frusto-conical engagement surface (47) of each of the faces and said annular members of a second type (46) consist of spherical balls through which a bore passes in a radial direction.

10. Device according to claim 1, wherein said annular members (33, 36, 38, 39, 40, 42, 43, 45, 46, 48) are made of rigid plastic material.

* * * * *